(12) United States Patent
Zerbe et al.

(10) Patent No.: US 6,231,957 B1
(45) Date of Patent: May 15, 2001

(54) RAPIDLY DISINTEGRATING FLAVOR WAFER FOR FLAVOR ENRICHMENT

(76) Inventors: Horst G. Zerbe, 82 Chemin Calais, Rigaud, Quebec (CA), J0P 1P0; Fadia Al-Khalil, 4 van Riper Ct., Lincoln Park, NJ (US) 07035

( * ) Notice: Subject to any disclaimer, the term of this patent is extended or adjusted under 35 U.S.C. 154(b) by 0 days.

(21) Appl. No.: 09/306,262

(22) Filed: May 6, 1999

(51) Int. Cl.$^7$ ........................................................ B32B 7/02
(52) U.S. Cl. ........................ 428/220; 428/332; 428/336; 428/339; 427/381; 427/384; 427/391.1; 427/411; 427/444
(58) Field of Search ..................... 424/435, 436, 424/437, 443; 428/220, 332, 333, 336, 339; 427/381, 379, 384, 388.4, 398.1, 411, 439, 444

(56) References Cited

U.S. PATENT DOCUMENTS

| | | | |
|---|---|---|---|
| Re. 33,093 | 10/1989 | Schiraldi et al. | 424/676 |
| 3,753,732 | * 8/1973 | Boroshok . | |
| 4,136,145 | 1/1979 | Fuchs et al. | 264/164 |
| 4,136,162 | 1/1979 | Fuchs et al. | 424/27 |
| 4,713,239 | 12/1987 | Babaian et al. | 424/81 |
| 4,842,854 | 6/1989 | Babaian et al. | 424/81 |
| 4,921,695 | 5/1990 | Babaian et al. | 424/81 |
| 4,925,670 | 5/1990 | Schmidt | 424/443 |
| 5,234,957 | 8/1993 | Mantelle | 514/772.6 |
| 5,332,576 | 7/1994 | Mantelle | 424/443 |
| 5,354,551 | 10/1994 | Schmidt | 424/49 |
| 5,446,070 | 8/1995 | Mantelle | 514/772.6 |
| 5,462,749 | 10/1995 | Rencher | 424/484 |
| 5,700,478 | 12/1997 | Biegajski et al. | 424/434 |
| 5,948,430 | 9/1999 | Zerbe . | |

FOREIGN PATENT DOCUMENTS

| | | |
|---|---|---|
| 601478 | 9/1987 | (AU) . |
| 7549696 | 3/1997 | (AU) . |
| 2148159 | 8/1972 | (DE) . |
| 0109269 | 11/1983 | (EP) . |
| 0273069 | 12/1986 | (EP) . |
| 0452446 | 10/1990 | (EP) . |
| 853378 | 11/1960 | (GB) . |
| 2048642 | * 12/1980 | (GB) . |
| 9820862 | 5/1998 | (WO) . |

* cited by examiner

*Primary Examiner*—Merrick Dixon
(74) *Attorney, Agent, or Firm*—Price, Heneveld, Cooper, DeWitt & Litton

(57) ABSTRACT

A sheet-shaped flavored film that rapidly disintegrates when placed on the surface of certain substrates and releases a natural or artificial flavor to the substrate to enhance or modify the intrinsic flavor of the substrate is provided. The flavored film includes one or more water-soluble polymers, one or more surfactants, and one or more flavoring agents. The flavored film has numerous applications in the food and food service industry wherein an easy to use, inexpensive and reproducible method of flavoring food products is desired.

20 Claims, No Drawings

RAPIDLY DISINTEGRATING FLAVOR WAFER FOR FLAVOR ENRICHMENT

BACKGROUND OF THE INVENTION

A broad variety of food products and other consumer products requires the addition of artificial and/or natural flavors in order to either add a certain taste and/or odor to the product, or to enhance its intrinsic flavor of the product, or to modify it. Also, flavors are commonly being added to products that naturally contain flavors in order to satisfy the desire of the consumer for products with precise taste reproducibility. In other cases, a food product, if prepared according to its standard method of preparation, may lack of certain taste characteristics that may be desired by the consumer. For example, a hamburger product that is being prepared using a hot steel plate will not acquire the taste of grilled meat which is usually only achieved by flame-broiling the product.

Numerous other applications in the food and food service industry demonstrate the desire for an easy-to-use, cheap, and reproducible method of flavoring food products or intermediates. In the case of pre-manufactured pizza dough, there is a need to add natural or artificial garlic flavor or other pizza flavors to the dough.

In the case of pre-manufactured fruitcakes, a number of problems is encountered that so far have not been resolved successfully: fruits that are used as toppings for fruit cakes are natural products and therefore exhibit a natural variability in their content of flavor components. In order to provide the customer with a product that always exhibits the same taste characteristics, there is a need to add flavor to the product, or to enhance or modify the initial flavor. However, when the fruit mix is applied to the surface of the dough, the moisture of the fruit mix upon storage migrates into the dry dough causing it to become soggy.

The same problem is being encountered during the production of ice cream products: Certain ice cream products involve waffles to sandwich the ice cream. Upon storage, the waffles tend to become soggy, thus making the product less attractive.

Various attempts have been made to overcome these problems: It has been tried to apply artificial grill flavor to hamburger products by sprinkling the flavor oil directly onto the hamburger. Also, it has been tried to formulate the artificial grill flavor into a paste and apply this flavor-containing paste onto the hamburger using a caulking gun. Yet another attempt to solve the problem involved spreading the flavor oil, or a paste containing the flavor oil on the hamburger using a spatula, knife, or similar tools.

However, all techniques that have so far been used to solve the above problem show significant disadvantages that limit their applicability or even prevent them from being used in a professional restaurant environment. They are either too complicated and, when applied by the restaurant personnel, bear the risk of insufficient and uneven distribution of the flavor on the product. When using these techniques, the quantity of flavor applied to the hamburger may vary significantly, thus causing unacceptable taste variations in the product. Since in the fast-food industry product acceptance and brand identification are closely associated with a precise reproducibility of the taste, these techniques do not provide an acceptable solution to the problem. More importantly, the process of applying the flavor by manually spreading or sprinkling it on the product is slow and increases the manufacturing cost of the product which represents a significant disadvantage in the highly competitive fast-food industry.

The attempts to add garlic flavor or other pizza flavors to pre-manufactured pizza dough by directly formulating it into the dough have been unsuccessful, either because the packaging materials are not sufficiently resistant to permeation of the flavor, or because the garlic flavor has been altered under the storage conditions of the products in the retail store. An additional advantage of formulating the garlic or pizza flavor into a wafer according to the present invention may be that the moisture from the topping will be held back thus preventing it from migrating into the dough and making it soggy. The same beneficial effect of the wafer according to the present invention of preventing moisture to migrate into the substrate may be favorably used to prevent the waffles of ice cream sandwiches to become soggy.

While the use of mucoadhesive, more or less rapidly disintegrating films for delivering breathfreshening and/or other flavoring agents to the oral cavity is known in the field, the use of wafer-like films according to the present invention for adding or modifying or enhancing flavors in food, food service, cosmetic, or pharmaceutical products has hitherto not been disclosed. PCT/EP97/08520 and the corresponding U.S. application Ser. No. 08/904,607 disclose rapidly dissolving films that can be adhered to the oral cavity thereby releasing cosmetically active agents like breathfreshening agents, said film comprising of water-soluble polymers, one or more polyalcohols, and cosmetically or pharmaceutically active agents. Optionally, the film may contain plasticizers or surfactants, flavors, flavor enhancers, or other ingredients commonly being used to modify or enhance the flavor of compositions commonly used for application to the oral cavity. In a similar way, U.S. Pat. No. 5,700,478 discloses pressure-sensitive adhesives that may adhere to mucosal surfaces and that are intended to release breathfreshening agents to the oral cavity. Other films that disintegrate under the influence of water can be used for purposes like dental cleansing, as described in EP 0 452 446 B1.

The use of wafer-like films to improve certain properties of food products is known in the field. U.S. Pat. No. 3,753,732 describes the use of a wafer that is intended to be used for bakery enrichment. It is made by adding starch to certain nutrients and compressing the mixture to wafer-like tablets which may then be used for bakery enrichment.

EP 0 273 069 A1 describes edible films consisting of neutral polysaccharides and polyalcohols that can be eaten directly, but when placed on the surface of certain food products, can prevent moisture from migrating into the substrate, or alternatively keep fragrances and/or seasoning agents in the food item. However, none of the techniques so far disclosed provide a satisfactory solution to the above problem, or contemplates the use of a wafer-like flavor film product according to the present invention to add flavor(s) to a food, food service, cosmetic, or pharmaceutical product, or to enhance or modify the intrinsic flavor of such products.

SUMMARY OF THE INVENTION

The present invention contemplates a more or less rapidly disintegrating sheet-shaped, wafer-like flavor film that, when placed on the surface of food, food service, cosmetic, or pharmaceutical products, disintegrates at a predetermined rate, thereby releasing the natural or artificial flavor to the food, cosmetic, or pharmaceutical products thus adding a certain desired taste and/or odor to the substrate, or enhancing or modifying the intrinsic flavor of the substrate. Optionally, the film may be used to prevent moisture from migrating into the food, food service, cosmetic, or pharmaceutical product.

The film is manufactured using conventional coating and drying techniques, cut into pieces of a shape and size that meet the requirements of the intended application, and packaged into suitable containers.

DETAILED DESCRIPTION OF THE INVENTION

While this invention is susceptible to embodiment in many different forms, preferred embodiments of the invention are shown. It should be understood, however, that the present disclosure is to be considered an exemplification of the principle of this invention and is not intended to limit the invention to the embodiments illustrated.

A variety of polymers is known to be useful for the preparation of more or less rapidly disintegrating films. One type of material that is suitable to form films according to the present invention comprises water-soluble polymers. Preferred water-soluble polymers are water-soluble polyvinyl pyrrolidones. More preferred are polyvinyl pyrrolidones with a K-value between 20 and 90. Polyvinyl pyrrolidones with a K-value between 25 and 60 are particularly preferred. Hydroxyethyl cellulose, when combined with polyvinyl pyrrolidone at a ratio of 1:2–3:1, hydroxypropyl-methyl cellulose, when combined with polyvinyl pyrrolidone at a ratio of 1:4–4:1, and polyvinyl alcohol, when combined with polyvinyl pyrrolidone at a ration of 1:5–1:1, are also more preferred water-soluble polymers. Other optional water-soluble polymers, without limiting the invention, include hydroxypropyl cellulose, carboxymethyl cellulose, sodium alginate, guar gum, tragacantha, arabic gum, acacia gum, xanthan gum. A film according to the present invention may also contain water-dispersible polyacrylates, like carboxyvinyl copolymers, methylmethacrylate copolymer, or polyacrylic acid. Other optional polymers include water-swellable, but not water-soluble, crosslinked carboxyfunctional polymers, like polycarbophil.

The surfactants used to prepare a film according to the present invention are a mixture of nonionic surfactants. Preferable mixtures are combinations of a polyoxyethylene sorbitan fatty acid ester, a polyoxyethylene alkyl ether, or a polyoxyethylene castor oil derivative with one or more polyalcohols. More preferably, the mixture is comprised of a polyoxyethylene sorbitan fatty acid ester and glycerol. The HLB value of the polyoxyethylene sorbitan fatty acid ester should be greater than 10, but not exceed 20. Other optional polyalcohols are propylene glycol, polyethylene glycol, or other polyalcohols commonly used in food, food service, cosmetic, or pharmaceutical products.

The ratio of the polyoxyethylene sorbitan fatty acid ester and the polyalcohol should range between 100:1 and 10:1, and the total concentration of surfactants in the film should not exceed 30%. The surfactants solubilize the flavor components. In those cases, where the incorporation of the flavor components into the mixture is possible without the use of a surfactant, the use of surfactants is not required. This may be the case if flavor components are used that possess self-emulsifying properties. In the context of this invention, a flavor component is self-emulsifying if it forms a stable emulsion with the other components of the coating solution without the addition of surfactants.

Natural or artificial flavor components may include grill flavor, garlic flavor, pizza flavor, natural or artificial fruit flavors, or other artificial or natural flavors or spices commonly used in food, food service, cosmetic, or pharmaceutical products. The effect of these flavors may be enhanced using flavor enhancers like tartaric acid, vanillin, or the like.

A film according to the present invention is prepared by forming a coating solution, coating it onto a suitable carrier material, drying it, and cutting it into pieces of a size and shape suitable for the intended application of the film. Coating solutions according to the present invention are prepared using solvents that are compatible with the ingredients used for the film. The solvents must be acceptable for food, food service, cosmetic, and pharmaceutical products. Examples, without limitation, of compatible solvents include water, ethyl alcohol, isopropyl alcohol, or mixtures thereof. The procedure for the preparation of coating solutions according to the present invention is as follows: To a mixture of suitable solvents, the surfactant, polyalcohol, flavor component, and polyvinylpyrrolidone are added under continuous stirring using a suitable stirring device until a clear solution has been formed. To the clear solution, the water-soluble or water-dispersible polymer or mixture of water-soluble polymers is slowly added under continuous stirring until a clear and homogeneous solution has been formed.

The solution is coated onto a suitable substrate, dried, and cut into pieces of a size and shape suitable for the intended application. A variety of coating methods, such as Meyer rod, knife over roll, gravure, or reverse roll can be used to coat and oven-dry the film. These coating and drying techniques are known to the expert in the field. Suitable substrates include non-siliconized kraft-paper, non-siliconized polyethylene-terephthalate film, non-siliconized polyethylene film, or the like. Depending upon the intended application and the desired properties of the final product, the thickness of the dry film may vary. The thickness depends on the concentration of solids in the coating solution, the gap on the coating head, and on the web speed. It can vary between 10 and 250 $\mu$m.

The dry film is cut into pieces that are suitable for the intended application. The techniques to cut the dry film are known to the expert and may include roller dies, flat-bed cutting knives, or the like.

The present invention is further illustrated by the following examples.

EXAMPLE 1

70 g of Polysorbate 80 and 3 g of Glycerol are thoroughly mixed (Premix 1). In a separate container, 132 g of Hydroxypropyl methylcellulose 50 cps and 50 g of Hydroxypropyl methylcellulose 100 cps are also thoroughly mixed (Premix 2).

A mixture of 750 ml Ethanol and 2375 ml water is heated to 60° C. 73 g of Premix 1 are added slowly under continuous stirring. After a clear solution has been formed, 20 g of artificial grill flavor are added under vigorous stirring. After a clear solution has been formed, 105 g of Povidone 30 are added slowly under continuous stirring until a clear solution has again been formed. To the clear solution, 182 g of Premix 2 are added slowly under continuous stirring until a clear solution has been formed. The solution is then allowed to cool to room temperature and coated onto non-siliconized kraft paper or any other suitable carrier material using a knife-over-roll coater. The coating gap and the web speed are set such that a thickness of the dry film of 50–150 $\mu$m is achieved. The temperature settings on the oven depend on the length of the drying oven. The drying temperature has to be set to remove the solvents completely, or almost completely, from the film. The resulting film is peeled off the substrate and cut into pieces of a shape and size suitable for the intended use.

A piece of the film was placed onto the surface of a grilled hamburger and covered with the hamburger roll, adding the taste of grilled meat to the product.

EXAMPLE 2

100 g of Povidone 30 (Plasdone S-630, ISP), 100 g of Kollidon 30 and 75 g Polyvinylalcohol are thoroughly mixed (Premix 3). 2300 ml water are heated to 60° C. 275 g of Premix 3 are added slowly under continuous stirring until a clear solution has been formed. To the clear solution, 150 g of Hydroxyethyl cellulose are added slowly under continuous stirring. The stirring is continued until a clear solution again has been formed. The solution is then allowed to cool to room temperature. Under vigorous stirring, 75 g of natural grill flavor (Givaudan-Roure) are added. The mixture is homogenized using a rotor/stator homogenizer until a stable emulsion has been formed.

The coating solution is coated onto non-siliconized kraft paper using a knife-over-roll coater or any other conventional coating and drying equipment. The coating gap and the web speed are set such that a thickness of the dry film of 50–150 μm is achieved. The temperature settings on the oven depend on the length of the drying oven. The drying temperature has to be set to remove the solvents completely, or almost completely, from the film. The resulting film is peeled off the substrate and cut into pieces of a shape and size suitable for the intended use.

EXAMPLE 3

Thoroughly mix 125 g of Plasdone S-630, 125 g of Kollidon 30 and 75 g of Polyvinylalcohol (Premix 4). Heat 2300 ml of water to 60° C. Slowly add 325 g of Premix 4 under continuous stirring until a clear solution has been formed. To the clear solution, slowly add 150 g of Hydroxypropyl methylcellulose 50 cps and continue stirring until a clear solution has been formed. Allow the solution to cool to room temperature. Under vigorous stirring, slowly add 25 g Natural Spiceolate Garlic (Givaudan Roure). Homogenize the mixture using a rotor/stator homogenizer.

The coating solution is coated onto non-siliconized kraft paper using the procedure as described in the previous example.

A piece of the film was placed on fresh pizza dough and covered with commonly used, yet garlic-free pizza toppings, adding the taste of fresh garlic to the baked pizza.

EXAMPLE 4

Thoroughly mix 125 g of Plasdone S-630, 125 g of Kollidon 30 and 75 g of Polyvinylalcohol (Premix 4). Heat 2300 ml of water to 60° C. Slowly add 325 g of Premix 4 under continuous stirring until a clear solution has been formed. To the clear solution, slowly add 150 g of Hydroxypropyl methylcellulose 50 cps and continue stirring until a clear solution has been formed. Allow the solution to cool to room temperature. Under vigorous stirring, slowly add 25 g Natural Spiceolate Pizza (Givaudan Roure). Homogenize the mixture using a rotor/stator homogenizer.

The coating solution is coated onto non-siliconized kraft paper using a knife-over-roll coater following the procedure as described in the previous example.

What is claimed is:

1. A sheet-shaped flavored film for the addition or modification of one or more flavors to food, said film being free of pharmaceutically and cosmetically active ingredients.

2. A flavored film according to claim 1, comprising at least one water-soluble polymer, at least one surfactant, and at least one flavoring agent.

3. A flavored film according to claim 1, wherein the water-soluble polymer is selected from the group consisting of hydroxyethyl cellulose, hydroxypropylmethyl cellulose, hydroxypropyl cellulose, polyvinyl pyrrolidone, carboxymethyl cellulose, polyvinyl alcohol, sodium alginate, polyethylene glycol, xanthane gum, tragacantha, guar gum, acacia gum, arabic gum, pregelatinized starch, polyacrylic acid, methylmethacrylate copolymer, carboxyvinyl copolymers, and mixtures thereof.

4. A flavored film accordingly to claim 3, wherein the composition of water-soluble polymers is not less than 60% by weight.

5. A flavored film accordingly to claim 2, wherein the surfactant is selected from the group consisting of polyoxyethylene sorbitan fatty acid ester, polyoxyethylene alkyl ether, polyalcohol, polyoxyethylene castor oil derivative, and a mixture thereof.

6. A flavored film accordingly to claim 5, wherein the polyalcohol is selected from the group consisting of glycerol, polyethylene glycol, and propylene glycol.

7. A flavored film accordingly to claim 2, wherein the flavor component is selected from the group consisting of grill flavor, garlic flavor, and pizza flavor.

8. A flavored film accordingly to claim 7, wherein the concentration of the flavor component in dry film is between 5 and 35% (w/w).

9. A method of preparing flavor films according to claim 1 comprising dispersing a flavor component in a solution of water-soluble polymers, coating and drying said dispersion onto a carrier material, separating the dry film from the carrier material, cutting the dry film into pieces of suitable size and packaging it into suitable containers.

10. A method according to claim 9, wherein the solvent used to dissolve the water-soluble polymer is selected from the group consisting of water, and a mixture of water and an organic solvent.

11. A method according to claim 10, wherein the organic solvent is selected from the group consisting of ethyl alcohol, isopropyl alcohol, acetone, and mixtures thereof.

12. A method according to claim 9, wherein the carrier material is selected from the group consisting of non-siliconized kraft paper, non-siliconized polyethyleneterephthalate, and a non-siliconized polyolefin.

13. A flavored film according to claim 2, wherein the dry film has a thickness of 20–500 μm.

14. A process for modifying the flavor of the food, comprising:

depositing a flavored film on the food, and disintegrating the film, thereby releasing a flavor to the food.

15. The process of claim 14, wherein the film comprises at least one water-soluble polymer, at least one surfactant, and at least one flavoring agent.

16. The process of claim 15, wherein the water-soluble polymer is selected from the group consisting of hydroxyethyl cellulose, hydroxypropylmethyl cellulose, hydroxypropyl cellulose, polyvinyl pyrrolidone, carboxymethyl cellulose, polyvinyl alcohol, sodium alginate, polyethylene glycol, xanthane gum, tragacantha, guar gum, acacia gum, arabic gum, pregelatinized starch, polyacrylic acid, methylmethacrylate copolymer, carboxyvinyl copolymers, and mixtures thereof.

17. The process of claim 15, wherein the film is comprised of at least 60% by weight of at least one water-soluble polymer.

18. The process of claim 15, wherein the surfactant is selected from the group consisting of polyoxyethylene sorbitan fatty acid ester, polyoxyethylene alkyl ether, polyalcohol, polyoxyethylene castor oil derivative, and a mixture thereof.

19. The process of claim 15, wherein the flavor component is selected from the group consisting of grill flavor, garlic flavor, and pizza flavor.

20. The process of claim 15, wherein the concentration of the flavor component in the film is from 5% (w/w) to 35% (w/w).

\* \* \* \* \*